(12) United States Patent
Kroll et al.

(10) Patent No.: US 7,866,470 B2
(45) Date of Patent: Jan. 11, 2011

(54) CARRY CASE FOR A PORTABLE ANALYTE MEASURING DEVICE

(75) Inventors: Steffen Kroll, Halle (DE); Kirsten Hoppert, Halle (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 12/197,857

(22) Filed: Aug. 25, 2008

(65) Prior Publication Data

US 2009/0057188 A1  Mar. 5, 2009

(30) Foreign Application Priority Data

Aug. 28, 2007 (EP) .................... 07016807

(51) Int. Cl.
A61B 19/02 (2006.01)
B65D 71/00 (2006.01)
B65D 30/22 (2006.01)

(52) U.S. Cl. .................... 206/438; 206/569; 383/38

(58) Field of Classification Search ......... 206/363–370, 206/438, 569–572, 305, 320; 383/38–40
See application file for complete search history.

(56) References Cited

U.S. PATENT DOCUMENTS

| | | | | |
|---|---|---|---|---|
| 2,112,406 A | * | 3/1938 | Metro | 383/38 |
| 2,324,194 A | * | 7/1943 | Campiglia | 206/570 |
| 2,731,142 A | * | 1/1956 | Miley | 383/7 |
| 4,086,945 A | * | 5/1978 | Carter | 383/38 |
| 4,212,377 A | * | 7/1980 | Weinreb | 383/38 |
| 4,819,793 A | * | 4/1989 | Willard et al. | 383/38 |
| 5,544,745 A | * | 8/1996 | Famorca | 206/320 |
| 6,602,469 B1 | | 8/2003 | Maus et al. | |
| 2003/0038047 A1 | | 2/2003 | Sleva et al. | |
| 2006/0040333 A1 | * | 2/2006 | Zocchi | 435/14 |
| 2006/0293577 A1 | * | 12/2006 | Morrison et al. | 206/569 |

FOREIGN PATENT DOCUMENTS

| | | |
|---|---|---|
| DE | 29920360 U1 | 11/2000 |
| DE | 29920361 U1 | 11/2000 |
| GB | 145977 | 7/1920 |
| WO | 2006023241 A1 | 3/2006 |

\* cited by examiner

*Primary Examiner*—Byron P Gehman
(74) *Attorney, Agent, or Firm*—Justin L. Sage; Roche Diagnostics Operations, Inc.

(57) ABSTRACT

A carry case is provided for a portable analyte measuring device, the carry case having opposing sides delimiting an interior space that is closed at one end and provided with an opening at the other end. According to certain embodiments of the present invention, the carry case is provided with an interior flap that is fastened at a distance from the closed end at one of the opposing sides and that can be swung from a first position in which a first side of the flap faces one of the opposing sides to a second position, in which the flap divides the interior space of the carry case and faces with the first flap side the closed end of the interior space.

8 Claims, 2 Drawing Sheets

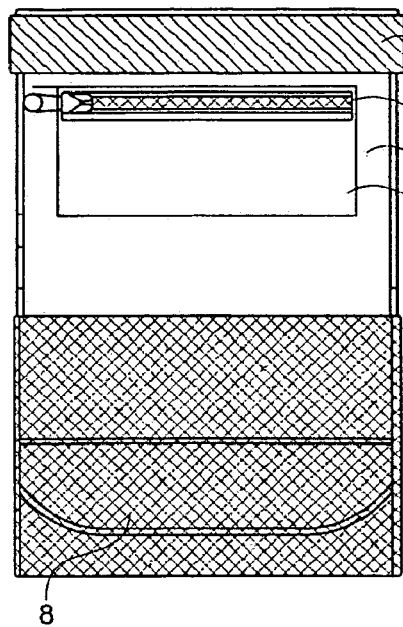
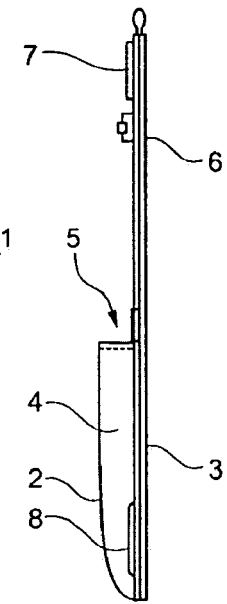
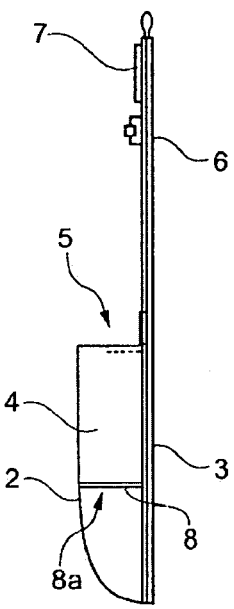
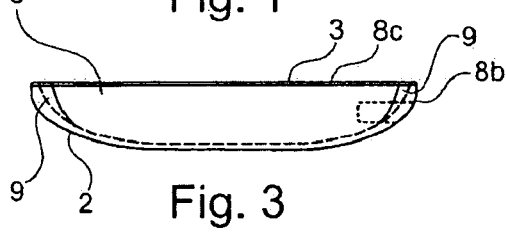
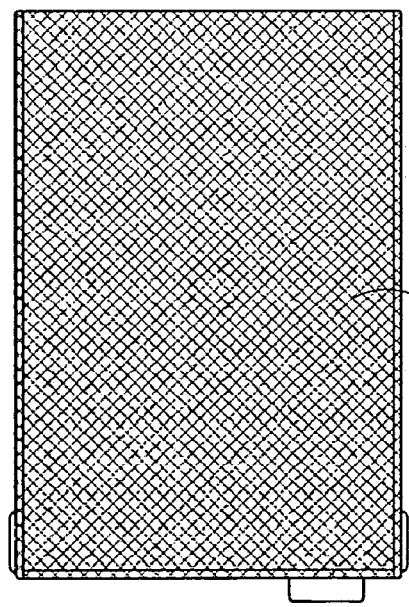
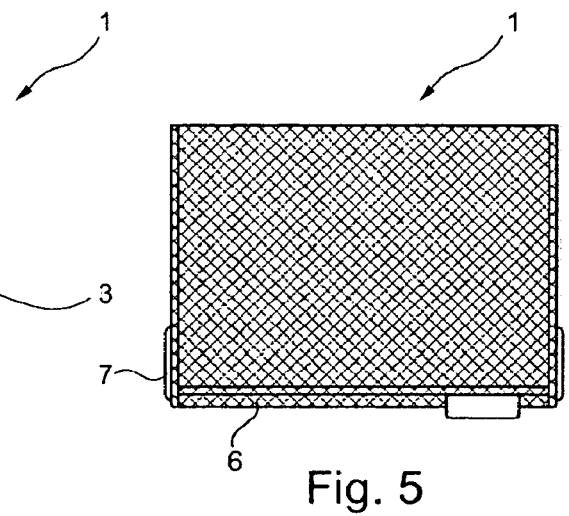

CARRY CASE FOR A PORTABLE ANALYTE MEASURING DEVICE

CLAIM OF PRIORITY

The present application is based on and claims priority to European Patent Application No. 07 016 807.5, filed Aug. 28, 2007, which is hereby incorporated by reference in its entirety.

TECHNICAL FIELD OF THE INVENTION

The present application relates to a carry case for a portable hand-held analyte measuring device, such as a blood glucose measuring device.

BACKGROUND

Portable hand-held medical devices, such as analyte measurement devices, are known, for example blood-sugar measuring devices used by diabetics. Many diabetics must measure their blood sugar level several times a day and therefore have to carry a blood-sugar measuring device along at all times as well as the required accessories and related consumable materials such as, e.g., testing elements, batteries and/or lancing devices and lancets. Therefore, carry cases for blood-sugar measuring devices are ideally as small and compact as possible in order facilitate the carrying along of a measuring device. Small and compact designs are also desirable for other analyte measurement devices that are typically carried along by common users of such devices.

The object of the invention is therefore to provide a carry case that makes it easier to the greatest possible extent to carry along portable analyte measuring devices and any possibly required consumable material.

SUMMARY

This object and others that will be appreciated by a person of ordinary skill in the art have been achieved according to the embodiments of the present invention disclosed herein. In one embodiment, the present invention comprises a carry case for a portable analyte measuring device, the carry case having opposing sides delimiting an interior space that is closed at one end and provided with an opening at the other end, wherein a flap that is fastened at a distance from the closed end at one of the opposing sides and that can be swung from a first position, in which a first side of the flap faces one of the opposing sides, to a second position, in which the flap divides the interior space of the carry case and faces with the first flap side the closed end of the interior space.

The object is also solved by a analyte measuring kit comprising a portable analyte measuring device, related consumable materials, and a carry case as described herein.

A carry case according to one embodiment of the present invention is provided with a flap which, when necessary, can divide the inside of the case in order to make room for the consumable material. Insofar as the flap of a carry case according to the invention, can be moved from a first position into a second position, it is possible to create room for the consumable material between the closed end of the inside of the case and the flap. The portable analyte measuring device can then be stored on the side of the flap facing the opening of the case.

Within the context of one embodiment of the present invention in which the portable analyte measuring device comprises a blood glucose measuring device, it is known that diabetics must carry with them a sufficient supply of consumable material in the case of a lengthy absence from their homes. Therefore, the conventional carry cases for blood glucose measuring devices can be unnecessarily large and bulky in the case of short absences of the diabetic from his home because there is typically provided a compartment for consumable material although this compartment is necessary only in the case of longer absences.

A carry case according to embodiments of the present invention remedies the situation in which the absence from home is shorter and a smaller supply of the consumable materials is needed. Should little or no consumable material be carried along in the case, the flap remains in its first position, so that the portable analyte measuring device can be pushed deeper into the case and, therefore, the case takes up less space. Should more consumable material be carried along, it will be placed in the case and, by means of the flap moved to the second position, it can be neatly stored between the closed end of the case and the flap. The portable analyte measuring device can then be stored safely between the flap and the opening of the inside of the carry case. This same arrangement is also useful in the context of other analyte measuring devices and their related consumables.

According to such embodiments, it is further helpful that the consumable materials placed in the carry case would be taken out only after the measuring device placed on the other side of the flap has been taken out, in view of the typical use case in which the consumable material is needed only at the same time as the measuring device, for example, to engage the material for use with the device.

In other embodiments, the distance between the closed end and the place at which the flap is fastened to one of the opposing sides is greater than the distance between an edge of the flap, with which the flap is fastened, and an opposite edge of the flap. In such a manner, the flap in its first position can be moved towards the closed end of the inside. When a portable analyte measuring device is pushed into an otherwise empty carry case, the flap is moved into the position that requires only a minimum of space.

In yet other embodiments, the flap in its, second position abuts with its edge the side of the carry case that is opposite the side provided with the flap.

Between the opposing sides that limit the internal space of the carry case there may other sides so that, by way of example, the inside of a carry case according to the invention can have a rectangular cross-section. In one embodiment, however, the opposing sides abut at their edges. By way of example, the edges could be welded, glued or, especially, sewn together.

In yet other embodiments, the opposing sides that delimit the interior space of the carry case abut each other seamlessly at the closed end of the inside. The easiest way to achieve this is by manufacturing the carry case out of a strip that is folded in such a manner that, on each side, its longitudinal edges are folded on top of each other and that they are there fastened to each other. Thus, the closed end of the inside can be configured as a folding edge of the strip. However, to manufacture the carry case it is also possible to place, e.g., two rectangular strips of cloth on top of each other and to join them in a continuous manner leaving merely an opening.

In yet other embodiments, the opposing sides are of different widths between their edges. For example, the side at which the flap is fastened can be only about 97% or less of the width of the opposing side. This brings about that the side at which the flap is fastened remains approximately flat while, because of its greater width, the opposing side arches towards the outside, so that the inside of the carry case has an approximately D-shaped or trapeze-shaped cross-section.

The inside of the carry case and its opening typically have a width extending along the opposing sides that exceeds the width of the flap measured in this direction. This feature makes it is easier to tilt the flap. In one embodiment, the inside extends beyond the two ends of the flap by, e.g., at least about 2 mm or more, and in other embodiments it extends beyond by about 3 mm or more.

A carry case according to the embodiments of the present invention is typically provided with a strap which, in order to close the inside, can be folded over its opening. With such a strap it is possible to adapt the effective size of a carry case depending on whether only a portable analyte measuring device or also consumable material are in it. Should the carry case contain only a portable analyte measuring device, it is possible to push it deeper into the case, such as to the closed end of the inside. Should the case also contain consumable material, the portable analyte measuring device cannot be pushed as deep into the case and might even protrude somewhat from the opening of the inside. A pliable strap adapts itself per se to such different conditions, for example by folding along a bending edge. The distance of such a bending edge to the opening can be variable and chosen depending on the actual circumstances. In such a manner, depending on how full the case is, the strap can, at a longer or shorter distance, cover one of the opposing sides of the case that delimit its interior space.

In other embodiments, the strap can be folded over the opening in various closing positions, which differ in how far the strap extends along the opposing sides. In one such embodiment, in a first closing position the strap covers at least two thirds of the length of the opposing sides, measured from the opening to the closed end of the inside, and in a second closing position the strap covers at the most one half of the length of the opposing sides. In another embodiment, in a first closing position the strap covers at least three fourths of the length of the opposing sides and in a second closing position the strap covers at the most a third of the length of the opposing sides.

In yet other embodiments, the strap is as wide as the side of the case from which the flap extends. For example, the length of the strap, measured from the opening to its free end, can be longer than the opposing sides of the carry case that delimit the interior space, whereby the length of the sides of the case is measured from the opening of the case up to the closed end of the inside. In one embodiment, the length of the strap is between about 8 cm and about 15 cm, and in other embodiments it is between about 10 cm and about 13 cm, or between about 11 cm and about 12.5 cm.

By way of example, the strap can be held by a loop when the carry case is closed. In one embodiment, the loop is fastened at the strap. In order to hold the strap in position, the loop can be turned over the opposing lateral walls that delimit the inside. By way of example, the loop can be a rubber-elastic strap, such as a textile strap.

In other embodiments, the length of the inside of the carry case, measured from its opening to its closed end, is not longer than about 12 cm, and in other embodiments is not longer than about 11 cm, and typically is between about 7 cm and about to 10 cm in length. In yet other embodiments, the width of the inside is not more than about 17 cm, and typically is between about 14 cm and about 16 cm in width. The dimension of the flap, measured from the side to which it is fastened to it free end, is typically at least 2 cm, and in certain embodiments is at least about 2.1 cm and can be between about 2.2 cm and about 2.8 cm.

The invention is to be explained in more detail by the following figures and examples.

BRIEF DESCRIPTION OF THE DRAWINGS

The following detailed description of the embodiments of the present invention can be best understood when read in conjunction with the following drawings, where like structure is indicated with like reference numerals and in which:

FIG. 1 shows a top view of an embodiment of a carry case according to the invention, in an open position.

FIG. 2a illustrates a cross sectional lateral view of the carry case of FIG. 1 showing an interior flap in a first position within the interior space.

FIG. 2b illustrates a cross sectional lateral view of a carry case showing an interior flap in a second position within the interior space for dividing the interior space.

FIG. 3 shows a cross-section of the inside of an embodiment of a carry case according to the present invention.

FIG. 4 shows a bottom view of the carry case of FIG. 1.

FIG. 5 shows an embodiment of a carry case according to the present invention in a closed position.

Figure 6:
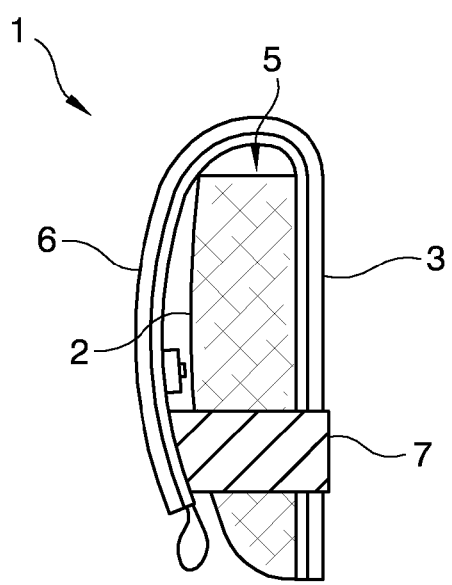
FIG. 6 shows a side view of an embodiment of a carry case according to the present invention in a closed position.

In order that the present invention may be more readily understood, reference is made to the following detailed descriptions and examples, which are intended to illustrate the present invention, but not limit the scope thereof.

DETAILED DESCRIPTION OF EMBODIMENTS OF THE PRESENT INVENTION

The following descriptions of the embodiments are merely exemplary in nature and are in no way intended to limit the present invention or its application or uses.

FIG. 1 shows a top view of a carry case 1 for a portable analyte measuring device; FIG. 2a shows a corresponding lateral view and FIG. 4 shows a bottom view. The carry case 1 has an interior space 4 delimited by the opposing sides 2, 3 of the case 1. The interior space is closed at one end and provided with an opening 5 on its opposite end. FIG. 3 shows a cross-section of the interior space 4.

The opening 5 of the interior space 4 can be closed with a strap 6 which, after closing, can be held in position with a loop 7. The strap 6 is as wide as the carry case's side 3 at which side it is fastened. In the illustrated embodiment, the loop 7 is an elastic textile strap that is fastened at the strap 6.

FIG. 5 shows the closed carry case 1, in which the strap 6 rests against one of the carry case's sides 2, 3 completely covering the side 2 while the case is empty or contains only a portable analyte measuring device. With the carry case being closed, the fuller the case 1 is, the less the pliable strap 6 extends along the case sides 2, 3.

In order to hold the strap 6 in position while the opening 5 is closed, the elastic strap 7 is led around the closed end of the interior space 4. It is, however, also possible to fasten the loop 7 at one of the lateral walls 2, 3. The strap 6 may have a narrow extension that can be inserted into a narrow loop. In the example shown the loop is as wide as the strap 6. It is also possible to provide the strap with a narrower extension.

In one embodiment of the illustrated carry case 1, the case comprises an interior flap 8 provided in the interior space 4 that is fastened at a distance from the closed end of the interior space 4 at one of the opposing sides, on side 3 in the illustrated embodiment. FIG. 2a shows the flap 8 in a first position in which it does not divide the interior space 4. FIG. 2b shows the flap in a second position in which it divides the interior space 4.

In the first position of the flap 8, a first side 8a of the flap 8 is facing one of the opposing sides, the side 3 in FIG. 2a, to which the flap 8 is fastened. The flap 8 can be swung from this first position to the second position that is shown in FIG. 2b. When the flap 8 is in the second position, it divides the interior space 4. The first flap side 8a is then facing the closed end of the inside 4.

In one embodiment, the flap 8a is provided in the first position, illustrated in FIG. 2a, when the carry case 1 is to carry a portable analyte measuring device with an additional supply of consumables for said device. When inserting the portable analyte measuring device into the interior space 4, the flap 8 is pushed into the position illustrated in FIG. 2a. Should a supply of consumables be carried in the interior space 4 of the case 1, such as, e.g., test elements for receiving a body fluid sample for the measuring of the blood sugar, lancets and/or batteries for a blood glucose measuring device, the flap 8 can be swung into the second position, illustrated in FIG. 2b; in which the flap 8 divides the interior space 4 so that consumable material can be stored between the closed end of the interior space 4 and the flap 8, and a portable analyte measuring device can be placed on the side of the flap 8 facing the opening 5. For the inserting of consumable material, the flap 8 is swung about 180° from the position illustrated in FIG. 2a, so that the first flap side 8a faces side 2 that is opposing side 3 to which the flap 8 is fastened.

In one embodiment, the interior space 4 of the carry case 1 has a generally D-shaped cross-section that is illustrated in FIG. 3. The interior flap 8 is approximately also D-shaped. The flap 8 is fastened on its straight edge. The distal edge of the flap opposite the fastened straight edge is generally rounded.

In one embodiment, the interior space 4 of the illustrated embodiment has a width measured along the opposing sides 2, 3 that is greater than the width of the flap 8 measured in this direction. Therefore the flap 8 can be swung easily within the interior space 4. In other embodiment, there is a small slot 9 in the flap 8. The slot 9 is located between the two ends of the flap 8 and the side 3 to which it is fastened. In one embodiment, the slot has a width between about 2 mm and about 5 mm. In the illustrated embodiment this slot 9 extends in the area where the rounding of the flap edge 8b begins. When the flap 8 is in the second position, illustrated in FIG. 2b, it touches both sides 2, 3.

In other embodiments, flap 8 is generally stiffer than the sides 2, 3 delimiting the interior space 4 and the strap 6. By way of example, the sides 2, 3 and the strap 6 can be made out of materials usually used for the manufacture of wallets such as, e.g., leather, imitation leather, plastics or textile fabrics. The same materials can be used for the outside materials of the flap 8 that, by way of example, may be stiffened by an inserted sheet out of, e.g., cardboard or plastic. In the illustrated embodiment, the outside of the sides 2, 3 are made out of PVC imitation leather that is covered with a textile fabric. Between these two layers inserts can be provided as, e.g., padding.

In the illustrated embodiment, the opposing sides 2, 3, that delimit the interior 4 of the carry case 1, touch each other at their edges where they are sewn together. The opposing sides 2, 3 and the strap 6 are formed by one strip that was folded along a folding line defining the end of the interior space 4, so that a section of its lateral sides lies against itself. In such a manner, the opposing sides 2, 3 border each other seamlessly at the closed end of the interior space 4.

In yet other embodiment, the strap 6 can be provided with an additional compartment 10 which, in the illustrated embodiment, is closed by means of, e.g., a zipper 11.

The above described carry case 1 comprises, together with a portable analyte measuring device and related consumable materials for use with the portable analyte measuring device, an analyte measuring system.

Dimensionally, embodiments of the strap 6 can have a length of about 12 cm, measured from the opening 5 to the free end. The interior space 4 can have a length of about 10 cm, measured from the closed end to the opening 5. The width of the opening 5 of the interior space 4 can be about 15 cm, with the width of the flap 8 being about 14 cm and the length of the flap 8 measured vertical to the width can be about 2.5 cm.

The features disclosed in the above description, the claims and the drawings may be important both individually and in any combination with one another for implementing the invention in its various embodiments.

It is noted that terms like "preferably", "commonly", and "typically" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

For the purposes of describing and defining the present invention it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

Having described the present invention in detail and by reference to specific embodiments thereof, it will be apparent that modification and variations are possible without departing from the scope of the present invention defined in the appended claims. More specifically, although some aspects of the present invention are identified herein as preferred or particularly advantageous, it is contemplated that the present invention is not necessarily limited to these preferred aspects of the present invention.

What is claimed is:

1. A carry case for a portable analyte measuring device, the carry case having first and second opposing sides delimiting an interior space that is closed at one end and generally accessible through an opening provided at the other end, the first and second opposing sides contacting each other at their respective edges, the carry case further comprising an interior flap having a proximal edge fastened within the interior space to the first opposing side at a distance generally spaced between the opening and the closed end, the interior flap being configured to swing from a first position in which a first side of the interior flap faces the first opposing side to a second position at which the interior flap divides the interior space of the carry case into a first compartment adjacent the opening and a second compartment adjacent the closed end, wherein the first side of the interior flap generally faces the closed end of the interior space when the interior flap is in the second position, the carry case further comprising a closing strap generally extending from the first opposing side proximate the opening, the closing strap being configured to fold over and generally cover the opening when in a closed position, the closing strap in the closed position extending adjacent and over most of the second opposing side exteriorly of the interior space and the closing strap having means for securing the closing strap in a position adjacent the second opposing side, wherein the first and second opposing sides and the closing strap comprise one or more generally pliable materials, and wherein the interior flap comprises material that is substantially stiffer than each of the first and second opposing sides.

2. The carry case according to claim 1, wherein the interior flap has a generally, rounded distal edge.

3. The carry case according to claim 1, wherein the interior space of the carry Case and its opening have a width extending across the first and second opposing sides that exceeds the width of the interior flap measured in the same direction.

4. The carry case according to claim 1, wherein the first and second opposing sides abut each other generally seamlessly at the closed end of the interior space.

5. The carry case according to claim 1, wherein the closing strap comprises a distal end which, when the closing strap is in the closed position, extends along the second opposing side greater or lesser lengths depending on the extent to which the interior space is filled.

6. The carry case according to claim 1, wherein the carry case is configured to carry a blood glucose measuring device in the first compartment and test elements for use with the blood glucose measuring device in the second compartment.

7. A portable analyte measuring system comprising a portable analyte measuring device, consumable material for use with the portable analyte measuring device, and a carry case having first and second opposing sides delimiting an interior space that is closed at one end and generally accessible through an opening provided at the other end, the carry case further comprising an interior flap having a proximal edge fastened within the interior space to the first opposing side at a distance generally spaced between the opening and the closed end, the interior flap being configured to swing from a first position in which a first side of the interior flap faces the first opposing side to a second position at which the interior flap divides the interior space of the carry case into a first compartment adjacent the opening and a second compartment adjacent the closed end, wherein the first side of the interior flap generally faces the closed end of the interior space when the interior flap is in the second position, the carry case further comprising a closing strap generally extending from the first opposing side proximate the opening, the closing strap being configured to fold over and generally cover the opening when in a closed position, the closing strap in the closed position extending adjacent and over most of the second opposing side exteriorly of the interior space and the closing strap having means for securing the closing strap in a position adjacent the second opposing side, wherein the consumable material is stored in the second compartment, and wherein the portable analyte measuring device is stored in the first compartment.

8. The system according to claim 7, wherein the portable analyte measuring device comprises a blood glucose measuring device and wherein the consumable material comprises one or more of test elements, lancets, and batteries.

\* \* \* \* \*